United States Patent [19]

Gasc et al.

[11] Patent Number: 4,988,692
[45] Date of Patent: Jan. 29, 1991

[54] 2,4-DIOXO-5-PHENYL-2,3,4,5-TETRAHYDRO-1H-1,5-BENZODIAZEPINES

[75] Inventors: Jean-Claude Gasc, Bondy; Daniel Humbert, Fontenay sous Bois, both of France

[73] Assignee: Roussel Uclaf, Paris, France

[21] Appl. No.: 457,237

[22] Filed: Dec. 27, 1989

[30] Foreign Application Priority Data

Dec. 29, 1985 [FR] France ............................. 88-17395

[51] Int. Cl.⁵ .................... C07D 243/12; A61K 31/55
[52] U.S. Cl. ...................................... 514/221; 540/518
[58] Field of Search ......................... 540/518; 514/221

[56] References Cited

PUBLICATIONS

Weber et al. "Liebigs Ann der Chemie" vol. 763, (1972) pp. 66–74.

Primary Examiner—Robert T. Bond
Attorney, Agent, or Firm—Bierman and Muserlian

[57] ABSTRACT

A compound in all possible isomeric forms and mixtures thereof of the formula

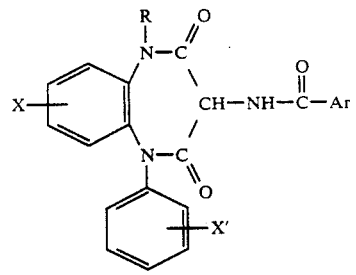

wherein X and X' are individually selected from the group consisting of hydrogen, halogen, cyano, —NO₂, —CF₃ and alkyl and alkoxy of 1 to 8 carbon atoms, R is hydrogen or alkyl of 1 to 8 carbon atoms and Ar is selected from the group consisting of an unsubstituted or substituted aryl of 6 to 14 carbon atoms, an unsubstituted or substituted aromatic heterocyclic or a heterocyclic united with an unsubstituted or substituted aryl having cholecystokinine antagonistic activity.

24 Claims, No Drawings

2,4-DIOXO-5-PHENYL-2,3,4,5-TETRAHYDRO-1H-1,5-BENZODIAZEPINES

STATE OF THE ART

Related literature are Justus Liebigs Annalen der Chimie., Vol. 763 (1972), p. 66 to 74 and J. of Org. Chem., Vol. 52 No. 5 (1987), p. 955 to 957.

OBJECTS OF THE INVENTION

It is an object of the invention to provide the novel compounds of formula I and a novel process and intermediates for their prepartion.

It is another object of the invention to provide novel cholecystokinine antagonistic compositions and a novel method of inducing cholecystokinine antagonistic activity in warm-blooded animals.

These and other objects and advantages of the invention will become obvious from the following detailed description.

THE INVENTION

The novel compounds of the invention are compounds in all possible isomeric forms and mixtures thereof of the formula

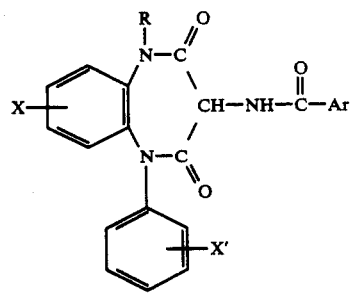

wherein X and X' are individually selected from the group consisting of hydrogen, halogen, cyano, —NO$_2$, —CF$_3$ and alkyl and alkoxy of 1 to 8 carbon atoms, R is hydrogen or alkyl of 1 to 8 carbon atoms and Ar is selected from the group consisting of an unsubstituted or substituted aryl of 6 to 14 carbon atoms, an unsubstituted or substituted aromatic heterocyclic or a heterocyclic united with an unsubstituted or substituted aryl.

X and X' can be in any position on the phenyl nuclei and when X or X' is halogen, it is preferably chlorine or bromine. When X or X' is alkyl or alkoxy, it is preferably methyl, ethyl, methoxy or ethoxy. When R is alkyl, it is preferably methyl, ethyl, n-propyl, isopropyl or n-butyl.

When Ar is aryl, it is preferably phenyl optionally substituted by at least one substituent selected from the group consisting of halogen such as chlorine or bromine, alkoxy of 1 to 4 carbon atoms such as methoxy or ethoxy, alkyl of 1 to 8 carbon atoms such as methyl or ethyl. When Ar is aromatic heterocyclic, it is preferably pyridinyl, thiophenyl, oxazolyl or isoxazolyl. When Ar is heterocyclic united with a phenyl nucleus, it is preferably an indolyl, benzofuranyl or quinolinyl nucleus.

Among the preferred compounds of formula I are those wherein R is alkyl of 1 to 4 carbon atoms such as methyl, those wherein X' is hydrogen, those wherein X is hydrogen or halogen such as chlorine in the 7-position.

The novel process of the invention for the preparation of compounds of formula I comprises reacting a compound of the formula

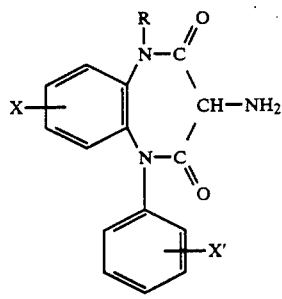

wherein R, X and X' have the above definitions with an acid or an acid derivative of the formula

wherein Ar has the above definition to obtain the corresponding compound of formula I. Preferably, the compound III is used in the form of acid, acid chloride or acid anhydride.

The compounds of formula II used as starting products are new products and are an object of the present invention. The compounds of formula II can be prepared by reacting a compound of the formula

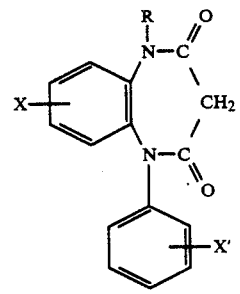

with an agent capable of introducing a =NOH for example the nitrile of amyl, isoamyl, isopentyl or tert-butyl to obtain the compound of formula

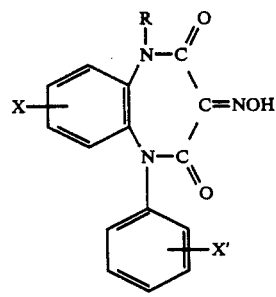

which is subjected to the action of a reduction agent, for example hydrogen in the presence of a catalyst such as Raney's nickel, or palladium on charcoal, or also of another reduction agent, for example Li AlH$_4$ or also zinc in acetic acid or sodium in ethanol to obtain the corresponding compound of the formula

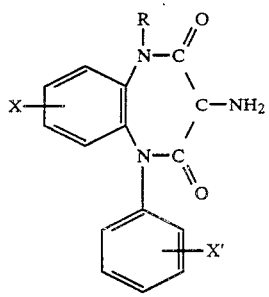

When it is desired to prepare resolved compounds of formula II, a variant of the process can be used comprising reacting a compound of the formula

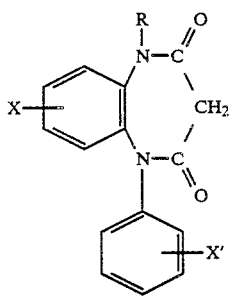

with a halogenation agent to obtain a compound of the formula

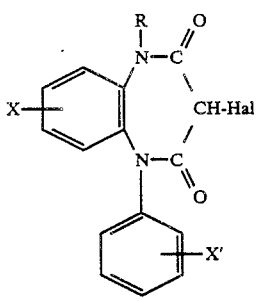

which is subjected to the action of a compound of the formula

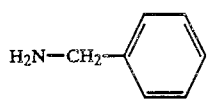

to obtain a compound of the formula

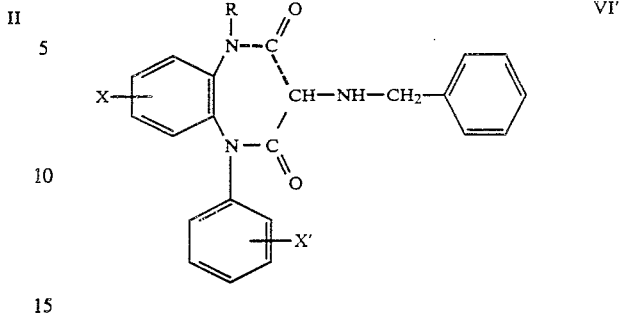

which is subjected to the action of a reduction agent to obtain a compound of the formula

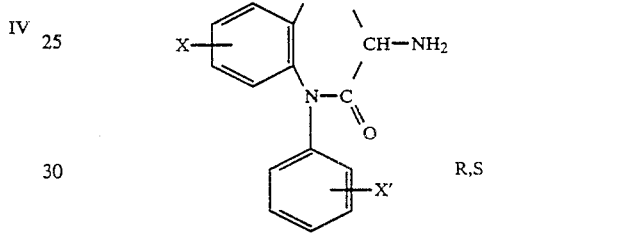

which is subjected to the action of a compound of the formula

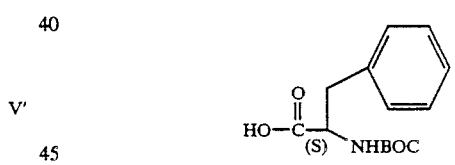

to obtain the compound of the formula

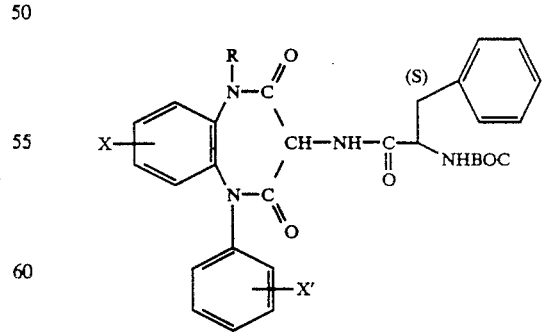

which is subjected to the action of an acid such as hydrochloric acid or trifluoroacetic acid to obtain the compound of the formula

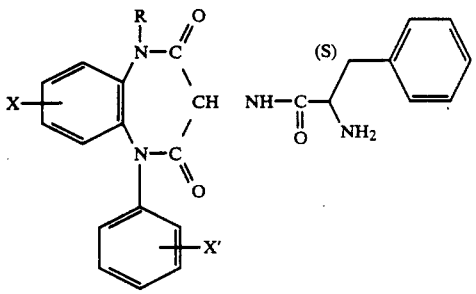

The 2 diastereoisomers are separated and each of the two compounds obtained is subjected to Edman's degradation to give the two enantiomers of the compound of formula II The novel cholecystokinine antagonistic compositions of the invention are comprised of an cholecystokinine antagonistically effective amount of at least one compound of formula I and an inert pharmaceutical carrier. The compositions may be in the form of tablets, dragees, capsules, granules, suppositories and injectable solutions or suspensions.

The compositions are agonists or antagonists of cholecystokinine of which the bonding sites have been shown to be at the central and peripheral levels. Cholecystokinine is a peptide widely distributed in the brain, particularly in the cortex, the striatum, the hippocampus, the ventral tegmentum, the septum and the hypothalamus. Cholecystokinine is also secreted at peripheral level by the small intestine, its action is shown in particular by the stimulation of vesicular contraction, an increase in biliary secretion, control of the enzymatic secretion of the pancreas, an action on gastric contractions, an action on intestinal motility. It can in some cases act on the arterial pressure and influence the immune systems.

Cholecystokinine co-exists in some central neurones with dopamine. It also intervenes in mechanisms involving acetylcholine, gaba, serotonin, opioids, somatostatin, substance P and ionic channels. Its administration causes physiological modifications: palpebral ptosis, hypothermia, hyperglycemia, catalepsy; and behavioural modifications: hypolocomotricity, decrease in exploration, analgesia, action in learning, modification of sexual behavior and satiety. Depending on the dose, it behaves as a dopaminergic agonist or antagonist.

The compositions can therefore be used in the treatment of certain disorders of alimentary functions, obesity, behavioral, emotional, sexual and memory disorders, schizophernia, and various disorders of the gastrointestinal area.

Examples of suitable excipients are talc, gum arabic, lastose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

The novel method of the invention for inducing cholecystokinine antagonistic activity in warm-blooded animals, including humans, comprises administering to warm-blooded animals a cholecystokinine antagonistically effective amount of at least one compound of formula I. The compounds may be adminstered orally, rectally or parenterally. The usual daily dose is 0,00066 to 1,33 mg/kg depending on the condition treated, the specific compound and the method of administration.

In the following examples there are described several preferred embodiments to illustrate the invention. However, it is to be understood that the invention is not intended to be limited to the specific embodiments.

EXAMPLE 1

N-(7-chloro-2,4-dioxo-1-methyl-5-phenyl-2,3,4,5-tetrahydro-1H-1,5-benzodiazepin-3-yl)-1H-indole-2-carboxamide STEP A:
7-chloro-1-methyl-5-phenyl-1H-1,5-benzodiazepin-2,3,4(5H)-trione 3-oxime 3 g of 7-chloro-1-methyl-5-phenyl-1H-1,5-benzodiazepine-2,4(3H,5H)-dione were suspended in 30 ml of tert-butanol and 1.12 g of potassium tert-butylate were added in small fractions. While maintaining the temperature at 20° C. with a water bath, 2.3 ml of tert-amyl nitrite were added and the solution thickened and a precipitate formed. After standing for 16 hours at ambient temperature, the precipitate formed was separated off (potassium salt of the oxime) and dissolved in 20 ml of water and acidified by acetic acid. The precipitate formed was extracted and the organic phase was washed with water, dried and concentrated to obtain 2.8 g of the expected product (yield=85%) melting at approx. 50° C.

Analysis

Calculated: % C 58.28; % H 3.67; % N 12.74; % Cl 10.75;
Found: 58.1; 3.9; 12.8; 10.6

STEP B:
3-amino-7-chloro-1-methyl-5-phenyl-1H-1,5-benzodiazepine-2,4(3H,5H)-dione 560 mg (1.7 mmole) of the oxime of Step A were hydrogenated in the presence of about 500 mg of Raney's nickel in 30 ml of ethanol under a pressure of 800 mbars for 16 hours. The catalyst were filtered off and the solvent was concentrated, and taken up in 20 ml of $CH_2Cl_2$. The organic phase was washed with water, dried over $MgSO_4$ and the solvent was eliminated to obtain 400 mg of the expected product in the form of a resin (yield=23%).

Analysis

Calculated: % C 60.86; % H 4.47; % N 13.31; % Cl 11.23,
Found: 61.12; 4.5; 12.9; 11.2

STEP C:
N-(7-chloro-2,4-dioxo-1-methyl-5-phenyl-2,3,4,5-tetrahydro-1H-1,5-benzodiazepin-3-yl)-1H-indole-2-carboxamide A mixture of 1.58 g (5 mmoles) of 3-amino-2,4-dioxo-7-chloro-1-methyl-5-phenyl-2,3,4,5-tetrahydro-1H-1,5-benzodiazepine, 0.89 g of 2-indol carboxylic acid, 1.05 g of 1-ethyl-3-(3-dimethylamino)-propyl carbodiimide, 1.02 g of 1-hydroxy benzotriazole and 50 ml of dichloromethane was stirred at ambient temperature for 18 hours and the precipitate formed was separated and washed with dichloromethane to obtain 1.36 g of the expected product melting at about 280° C. (yield 59%)

Analysis
Calculated: % C 65.43; % H 4.17; % N 12.21; % Cl 7.72,
Found: 65.42; 4.0; 12.3; 8.1
EXAMPLES 2 to 6
Using the procedure of Example 1 and by following the reaction scheme:
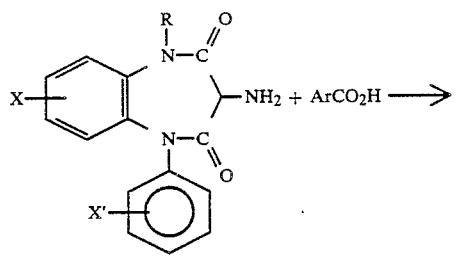 + ArCO$_2$H ⟶
-continued
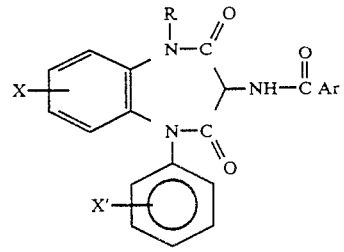
the following products were obtained.
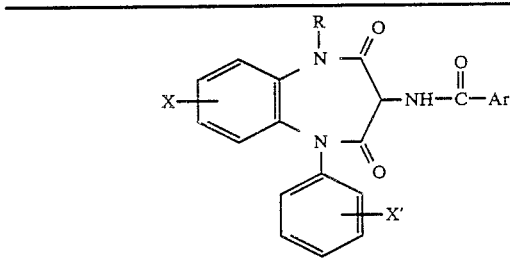
| Ex. | R | X | X' | Ar | Stereo-chemistry | Physical constant |
|---|---|---|---|---|---|---|
| 2 | CH$_3$ | H | H | 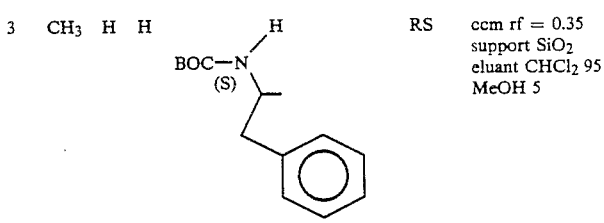 | R or S | M.p. = 170° C. |
| 3 | CH$_3$ | H | H | 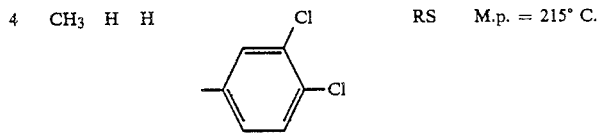 | RS | ccm rf = 0.35 support SiO$_2$ eluant CHCl$_2$ 95 MeOH 5 |
| 4 | CH$_3$ | H | H | 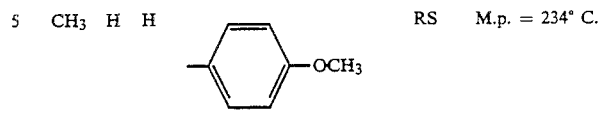 | RS | M.p. = 215° C. |
| 5 | CH$_3$ | H | H | 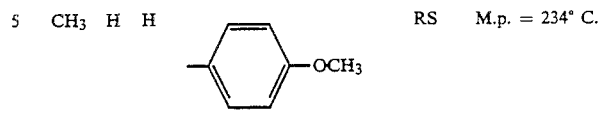 | RS | M.p. = 234° C. |
| 6 | CH$_3$ | H | H | 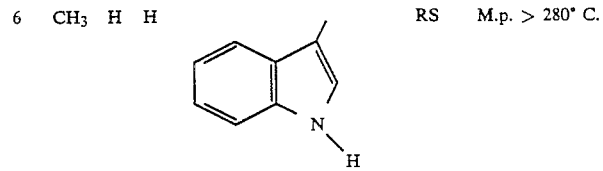 | RS | M.p. > 280° C. |

Preparation 1:
3-amino-1-methyl-5-phenyl-1H-1,5-benzodiazepine-2,4-(3H, 5H)-dione

STEP A:
1-methyl-5-phenyl-1H-1,5-benzodiazepine-2,4-(3H, 5H)-dione

A suspension of 103 g of clobazam, 1 liter of methanol, 23 g of potassium hydroxide in solution in 400 ml of methanol and 50 g of Raney's nickel washed beforehand with water and with methanol, was hydrogenated for 24 hours under a pressure of 800 mbars. 1 liter of methylene chloride was added and the catalyst was filtered off. The solvents were concentrated under reduced pressure and the residue was taken up in methylene chloride. The mixture was washed with water, dried over magnesium sulfate and concentrated under reduced pressure. The product obtained was crystallized from methanol, washed with ether and dried to obtain 76.69 g of the sought product melting at 173° C.

STEP B:
3-bromo-1-methyl-5-phenyl-1H-1,5-benzodiazepine-2,4-(3H, 5H)-dione

While irradiating with a 500 watt lamp at about 40° C., a solution of 5 ml of bromine and 30 ml of carbon tetrachloride was introduced dropwise into a solution of 25 g of the product of Step A and 750 ml of carbon tetrachloride. At the end of the introduction, the lamp was extinguished, the mixture was cooled and 500 ml of methylene chloride were added. The organic phase was washed with a saturated sodium carbonate solution, then with water and the product obtained was chromatographed on silica. Elution with an ethyl acetate-methylene chloride mixture 7-3-yielded 10.5 g of the sought product melting at 132° C.

STEP C:
1-methyl-5-phenyl-3-{(phenylmethyl)-amino}-1H-1,5-benzodiazepine-2,4(3H, 5H)-dione A mixture of 50 mg of the product of Step B and 2 ml of benzylamine was heated at 100° C. for 3 hours and the reaction medium was poured into water. The product obtained was separated, washed, and dried in the presence of phosphoric anhydride to obtain 50 mg of the sought product.

NMR CDCl$_3$ ppm

H of benzyl CH$_2$ 3.86 ppm

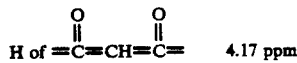  4.17 ppm

STEP D:
3-amino-1-methyl-5-phenyl-1H-1,5-benzodiazepine-2,4-(3H, 5H)-dione 3.1 g (8.4 mmoles) of the benzylamine of Step C in 100 ml of methanol was hydrogenated under 1800 mb of pressure in the presence of 900 mg of 10% palladized charcoal. After absorption of the expected quantity of hydrogen, the catalyst was filtered off and the methanol was concentrated to dryness to obtain a white powder which was crystallized from ethanol to provide 1.67 g of the expected amine melting at 186° C.

IR Spectrum: NH 3383-3321 cm$^{-1}$

STEP E: 1,1-dimethylethyl (S) {2{(2,4-dioxo-1-methyl-5-phenyl-2,3,4,5-tetrahydro-1H-1,5-benzodiazepin-3-yl)-amino}-2-oxo-1-(benzyl)-ethyl}-carbamate A mixture of 2.4 g of the product of Step D, 40 ml of methylene chloride, 2.26 g (8.5 mmoles) of BOC-L-phenylalanine, 1.8 g (9.4 mmoles) of dicyclohexycarbodiimide and 1.26 g (8.5 mmoles) of 4-pyrrolidinopyridine was stirred for 16 hours. The mixture was poured into 100 ml of hydrochloric acid and the decanted organic phase was washed three times with water. After drying, the solvent was eliminated to obtain 5 g of a yellowish foam.

NMR: CDCl$_3$ ppm
BOC: 1.38 ppm (s)
φCH$_2$—CH: 3.03 and 3.27 ppm
N—CH$_3$ 3.55 ppm (s)

STEP F: ((αS) R*,S*)
α-amino-N-(2,4-dioxo-1-methyl-5-phenyl-2,3,4,5-tetrahydro-1H-1,5-benzodiazepin-3-yl)-benzene-propanamide Isomer A and isomer/(α(R*,R*): isomer B.

5 g of the product of Step E were dissolved in 80 ml of ethyl acetate and a dry hydrochloric acid current was passed through at 5° C. for 20 minutes. After returning to ambient temperature, the organic solution was washed with a saturated solution of sodium bicarbonate, then with a saturated solution of sodium chloride. After drying, the solvent was eliminated to obtain about 4.5 g of a yellow foam which was chromatographed on silica. Elution with a mixture of CH$_2$Cl$_2$: 89 MeOH: 10 AcOH:1 isolated the first isomer A, Weight=1.78 g, Rf=0.52; and the second isomer B, Weight=1.68 g, Rf=0.48.

STEP G:
3-amino-7-chloro-1-methyl-5-phenyl-1H-1,5-benzodiazepine-2,4(3H, 5H)-dione A mixture of 0.238 g of isomer A of Step F, 4 ml of methylene chloride, and 0.125 ml of phenyl isothiocyanate was stirred for one hour at ambient temperature. The solvent was concentrated and 3 ml of trifluoroacetic acid were added followed by stirring for one hour at ambient temperature and then concentration under reduced pressure. The residue was taken up in a methylene chloride-methanol mixture (1/1) to dissolve the gum formed and the solution was poured over 5 ml of concentrated ammonia. The mixture was stirred overnight at room temperature and was extracted with methylene chloride. The extracts were washed with water, dried and evaporated to dryness to obtain 40 mg of the desired optionally active amine in the form of a white resin.

CCM RF=0.23 Ethyl acetate-triethylamine 97/3.

In the same way, starting with isomer B of Step F, the second antipode was obtained.

EXAMPLE 7 TABLETS

Tablets were prepared containing 20 mg of the product of Example 3 and sufficient excipient of lactose, wheat starch, treated starch, rice starch, magnesium stearate and talc q.s. for a tablet of 300 mg.

EXAMPLE 8 CAPSULES

Capsules were prepared containing 50 mg of the product of Example 2 and sufficient excipient of talc, magnesium stearate and aerosil q.s. for a capsule of 300 mg.

BIOLOGICAL STUDY

(1) Central receptors

The cortices of 20 male rats weighing 150 to 200 g were removed, and were ground up with Polytron in sucrose 0.32M. After centrifuging, the supernatant was recovered and centrifuged. The residues were re-suspended in 120 ml of Hepes buffer pH 7.4 (Hepes 10 mM, NaCl 130 mM, $MgCl_2$, $6H_2O$ 5 mM, bacitracin 250 mg/l., PMSF 1 mg/l), and re-centrifuged. The residues were taken up in 120 ml of Hepes buffer pH 7.4 and re-centrifuged at 30,000 g for 30 minutes. The residues thus obtained were taken up in 500 ml of Hepes buffer pH 7.4, which enabled 240 aliquots of 2 ml of homogenate to be obtained. The incubation was effected at 25° C. for 30 minutes in the presence of 0.5 nM of 3H CCK8 and the test product (10,000 μM for 1 dose, or with a range of 7 doses or of cold CCK8 ($10^{-6}M$), which was the reference product). After returning the aliquots of the homogenate to 0° C., they were filtered on Whatman GF/B filters and the filters were washed with $3 \times 5$ ml of a Tris HCl 50 mM pH 7.4 buffer. The results are expressed is $IC_{50}$ which is the concentration necessary to inhibit by 50% the fixed specific radioactivity.

(2) Peripheral receptors

The pancreases of 3 male rats weighing 150-200 g were removed and ground up with Polytron (4 grindings, speed 3, with an interval of 10 seconds between the grindings) and the homogenate was filtered through a gauze and then centrifuged at 30,000 g for 30 minutes. The residues obtained were taken up in 400 volumes (600 ml) of Tris 50 mM HCl pH 7.4 buffer containing BSA 2 g/l., bacitracin 0.1 mM, $MgCl_2$ 5 mM, dithiothreitol 5 mM. 2 ml aliquots of the homogenate were incubated at 25° C. for 60 minutes in the presence of 0.2 mM 3H CCK8 and of the test product (10,000 μM for 1 dose, or with one range of 7 doses) and of cold CCK8 ($10^{-6}M$) which was the reference product. After returning to 0° C., the aliquots were filtered on Whatman GF/B filters, pre-washed in a solution of polyethylene imine at 0.05% and washed with $3 \times 5$ ml of buffer Tris HCl 50 mM, pH 7.4. The results were expressed in $IC_{50}$, the concentration necessary to inhibit by 50% the fixed specific radioactivity, $IC_{50}$ n mol

| Example | Peripheral CCK | Central CCK |
| --- | --- | --- |
| 1 | 20 | 2200 |
| 2 | 14 | >10000 |

ACTION ON THE ALIMENTARY INTAKE IN A RAT

The tests were carried out on groups of 5 rats weighing 250 g±10 g and the animals were individually placed in cages with a trough as described by Fregly (J. Appl. Physiol Vol. 15 (1960), p. 539) which avoided wasting of the powdered foodstuffs. The rats were accustomed to taking their daily portion over 5 consecutive hours with as much drinking water as desired being offered in glass feeding bottles. The quantities of food ingested were determined individually by the weight of the troughs and the comsumptions were followed hourly for 5 hours after intraperitoneal administration of 10 mg/kg of the compound. The quantities consumed are expressed in g/100 g of body weight per hour. The averages are compared to those obtained with control animals by a DUNNETT test.

Results

At a dose of 10 mg/kg per intraperitoneal dose, the product of Example 1 showed an anorexigenic activity as it significantly reduced the food consumption of the animals by more than 50% in relation to that of the control animals.

Action on the isolated ileum of a guinea-pig

The test was carried out on fragments of ileum from male guinea-pigs placed under a tension of 1 g in a Krebs solution aerated with carbogen and maintained at 37° C. The contractions were recorded with a microdynamometer connected to a polygraph. The ileum was left at rest for 30 minutes and then CCK8 was added to the bath in a concentration of $1.10^{-8}M$, followed by rinsing. The test product was added to the bath, left in contact with the organ for one minute and then CCK8 ($1.10^{-8}M$) was added to the bath. The possible antagonism was expressed by comparing the contractions caused by the CCK8 before and after contact with the product under test. The product of Example 2 at a dose of $10^{-7}M$ presented significant antagonist activity.

Various modifications of the products and method of the invention may be made without departing from the spirit or scope thereof and it should be understood that the invention is intended to be limited only as defined in the appended claims.

What we claim is:

1. A compound in all possible isomeric forms and mixtures thereof of the formula

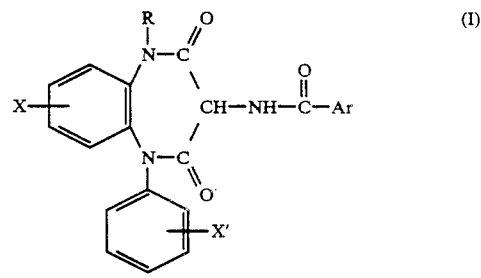

wherein X and X' are individually selected from the group consisting of hydrogen, halogen, cyano —$NO_2$, —$CF_3$ and alkyl and alkoxy of 1 to 8 carbon atoms, R is hydrogen or alkyl of 1 to 8 carbon atoms and Ar is selected from the group consisting of phenyl optionally substituted by at least one substituent selected from the group consisting of halogen, alkoxy of 1 to 4 carbon atoms, alkyl of 1 to 8 carbon atoms, pyridinyl, thiophenyl, oxazolyl or isoxazolyl, indolyl, benzofuranyl and quinolinyl.

2. A compound of claim 1 wherein R is alkyl of 1 to 4 carbon atoms.

3. A compound of claim 2 wherein R is methyl.

4. A compound of claim 1 wherein X' is hydrogen.

5. A compound of claim 1 wherein X is hydrogen.

6. A compound of claim 1 wherein X is halogen.

7. A compound of claim 6 wherein X is chlorine in the 7-position.

8. A compound of claim 1 selected from the group consisting of N-(7-chloro-2,4-dioxo-1-methyl-5-phenyl-2,3,4,5-tetrahydro-1H-1,5-benzodiazepin-3-yl)-1H-indole-2-carboxamide and N-(2,4-dioxo-1-methyl-5-phenyl-2,3,4,5-tetrahydro-1H-(1,5)-benzodiazepin-3-yl)-1H-indole-2-carboxamide.

9. A cholecystokinine antagonistic composition comprising a cholecystokinine antagonistically effective amount of at least one compound of claim 1 and an inert pharmaceutical carrier.

10. A composition of claim 9 wherein R is alkyl of 1 to 4 carbon atoms.

11. A composition of claim 10 wherein R is methyl.

12. A composition of claim 9 wherein X' is hydrogen.

13. A composition of claim 9 wherein X is hydrogen.

14. A composition of claim 9 wherein X is halogen.

15. A composition of claim 9 wherein X is chlorine in the 7-position.

16. A composition of claim 9 wherein the active compound is selected from the group consisting of N-(7-chloro-2,4-dioxo-1-methyl-5-phenyl-2,3,4,5-tetrahydro-1H-1,5-benzodiazepin-3-yl)-1H-indole-2-carboxamide and N-(2,4-dioxo-1-methyl-5-phenyl-2,3,4,5-tetrahydro-1H-(1,5)-benzodiazepin-3-yl)-1H-indole-2-carboxamide.

17. A method inducing cholecystokinine antagonistic activity in warm-blooded animals comprising administering to warm-blooded animals a cholecystokinine antagonistically effective amount of at least one compound of claim 8.

18. A method of claim 17 wherein R is alkyl of 1 to 4 carbon atoms.

19. A method of claim 18 wherein R is methyl.

20. A method of claim 17 wherein X' is hydrogen.

21. A method of claim 17 wherein X is hydrogen.

22. A method of claim 17 wherein X is halogen.

23. A method of claim 17 wherein X is chlorine in the 7-position.

24. A method of claim 17 selected from the group consisting of N-(7-chloro-2,4-dioxo-1-methyl-5-phenyl-2,3,4,5-tetrahydro-1H-1,5-benzodiazepin-3-yl)-1H-indole-2-carboxamide and N-(2,4-dioxo-1-methyl-5-phenyl-2,3,4,5-tetrahydro-1H-(1,5)-benzodiazepin-3-yl)-1H-indole-2-carboxamide.

* * * * *